United States Patent
Einy

(10) Patent No.: US 9,067,080 B2
(45) Date of Patent: Jun. 30, 2015

(54) METHOD AND APPARATUS OF REMOTELY-OPERATED AUTOMATED EXTERNAL DEFRIBRALLATOR INCORPORATED INTO A HANDHELD DEVICE

(71) Applicant: Gilad Einy, Haifa (IL)

(72) Inventor: Gilad Einy, Haifa (IL)

( * ) Notice: Subject to any disclaimer, the term of this patent is extended or adjusted under 35 U.S.C. 154(b) by 0 days.

(21) Appl. No.: 13/870,996

(22) Filed: Apr. 26, 2013

(65) Prior Publication Data

US 2014/0222095 A1    Aug. 7, 2014

Related U.S. Application Data

(63) Continuation-in-part of application No. 12/404,938, filed on Mar. 16, 2009, now abandoned.

(51) Int. Cl.

| A61N 1/00 | (2006.01) |
| A61N 1/39 | (2006.01) |
| G06F 19/00 | (2011.01) |
| H04M 1/21 | (2006.01) |
| H04M 1/725 | (2006.01) |

(52) U.S. Cl.
CPC ............. *A61N 1/3968* (2013.01); *A61N 1/3918* (2013.01); *A61N 1/39* (2013.01); *G06F 19/3406* (2013.01); *G06F 19/3418* (2013.01); *H04M 1/21* (2013.01); *H04M 1/72536* (2013.01); *H04M 2250/12* (2013.01); *H04M 2250/52* (2013.01); *A61N 1/3993* (2013.01)

(58) Field of Classification Search
CPC ...... A61N 1/39; A61N 1/3925; A61N 1/3993
USPC ....................................... 607/5; 600/508, 509
See application file for complete search history.

(56) References Cited

U.S. PATENT DOCUMENTS

| 6,546,232 B1 * | 4/2003 | Sack et al. .................... 455/90.1 |
| 7,433,718 B2 * | 10/2008 | Manabe et al. ............. 455/575.1 |
| 2004/0172069 A1 * | 9/2004 | Hakala ............................... 607/5 |
| 2006/0100533 A1 * | 5/2006 | Han et al. ....................... 600/508 |
| 2007/0021677 A1 * | 1/2007 | Markel ........................... 600/509 |
| 2007/0270909 A1 * | 11/2007 | Saketkhou ......................... 607/5 |

* cited by examiner

*Primary Examiner* — Christopher D Koharski
*Assistant Examiner* — Philip Edwards
(74) *Attorney, Agent, or Firm* — Haim M. Factor

(57) ABSTRACT

A rescue cell apparatus used for cardiac defibrillation of a patient, the apparatus comprising: a hand held device for sending and receiving communication signals and configured to be used as a remote control to administer a defibrillation pulse to the patient for cardiac defibrillation; a defibrillator unit having a sensor electronic pad positionable on the patient, the sensor electronic pad adapted to deliver the defibrillation pulse; and a second electronic pad, connectable by an electrical wire to the defibrillator unit, the second electronic pad positionable on the patient and adapted to detect ECG signals and to deliver the defibrillation pulse to the patient; and an image recognition module configured in the handheld device, and adapted to verify positioning of the sensor electronic pad and the second electronic pad on the patient before defibrillation.

9 Claims, 11 Drawing Sheets

METHOD AND APPARATUS OF REMOTELY-OPERATED AUTOMATED EXTERNAL DEFRIBRALLATOR INCORPORATED INTO A HANDHELD DEVICE

RELATED APPLICATION

The present application is a CIP application, claiming priority from U.S. patent application Ser. No. 12/404,938, filed 16 Mar. 2009, whose disclosure is incorporated herein by reference.

FIELD OF THE INVENTION

The present invention relates to a mobile, hand-held apparatus for providing a solution for reducing deaths caused by: heart attacks; Sudden Cardiac Arrest (SCA) caused by Ventricular Fibrillation (VF); and Ventricular Tachycardia (VT); which can be used by everyone, virtually everywhere, and at any time.

BACKGROUND OF THE INVENTION

In the US alone, over 500,000 people die annually from SCA. Many of these victims have no prior warning of heart disease, and 70% die outside the hospital. The most common electrophysiologic mechanisms leading to SCA are tachyarrhythmias such as VF or VT, and the only treatment for this victim is to provide an immediate, high-energy electric shock through the heart. Minimizing the time to first shock is critical since, the survival rates after cardiac arrest decrease by approximately seven to 10 percent every minute that defibrillation is delayed. If a shock is not applied within 10 minutes, the chances of resuscitation are almost zero.

Survival from sudden cardiac arrest critically depends on timely resuscitation. Chances for survival from sudden cardiac arrest caused by VF or VT will be achieved if Automated External Defibrillators (AED) were made more widely available within the community, ensuring that patient who had cardiac arrest in the out-of-hospital setting will be treated as soon as possible by this life saving technique.

It is estimated that approximately 50,000 of these deaths could have been prevented if an Automated External Defibrillator (AED) had been available for immediate use at the time of the emergency, and someone had initiated the Cardiac Chain of Survival.

The American Heart Association stresses the importance of creating "heart save community" by providing quick access to AEDs which are available to the public at airports, malls, sport stadiums and leisure centers, thus creating "heart save environment".

Commercially available AED systems were designed for use by people with no medical training (lay rescuers) and by health care providers. The AED system is attached to the patient's chest and it is used to analyze the patient's heart rhythm. If VF is detected, the AED delivers an electric shock to get the heart beating again. Such units have been placed in public locations such as airports, airplanes, and theaters. However, to date there is no device specifically designed for personal/laymen use.

The person operating an AED known in the art is potentially at risk of getting an electrical shock if he is in contact with the patient connected to the shocking electrodes. This risk increases when an untrained person is operating the AED.

U.S. Pat. No. 5,700,281, issued on Dec. 23, 1997, describes the use of prompts to guide a user in assisting an SCA victim. An AED is described to be used by an untrained user. Utilizing the electrode packaging above, the AED monitors the state of the AED and the stage of a rescue. In particular, at least five stages of a rescue are monitored. These include: 1) rescue initiated; 2) preparing victim; 3) applying electrodes; 4) AED in use; and 5) rescue completed. The '281 patent uses impedance values between the electrode pads to determine the stage of a rescue attempt in order to prompt and thereby guide the user.

United States Patent Application 20040143297, to Ramsey, Maynard III; titled "Advanced automatic external defibrillator powered by alternative and optionally multiple electrical power sources and a new business method for single use AED distribution and refurbishment"; filed Jan. 21, 2003; describes an AED being powered by 120/240 VAC electrical power alone, being powered by external DC power alone, or any in combination with or without internal-integral battery power, and further an AED access service business method for sales of access to AEDs. The AED, in addition to the defibrillator circuitry comprises a long, tangle free power access cord to be plugged into an external source of AC or DC power and optionally, additional sets of body surface and alternative electrodes positioned in the esophagus and/or heart. The AED has additional advanced capabilities including the ability to deliver rapid sequential shocks through one or more sets of patient electrodes, and the optional mode of shock delivery whereby the shock is delayed while the AED continues to analyze the patients ECG waveform and delays the defibrillation shock or sequence of shocks until the ECG analysis indicates conditions are optimum for successful defibrillation.

Currently most known AED systems are big and heavy to carry and are available for use by the public at airports, malls, sport stadiums and leisure centers. The AED systems are not designed for personal use; they do not include any communication system; and none of them use a remote control for the safety of the person who is using them.

The FRED Easyport AED from Schiller weighs 490 grams. According to the manufacturer, the device intended for use by basic life support responders, healthcare professionals, such as doctors, paramedics and public service staff. Additionally, at-risk heart patients could carry this device for their own rescue after they and their family are trained in its use.

SUMMARY OF THE INVENTION

The present invention relates to a mobile, hand-held apparatus for providing a solution for reducing deaths caused by: heart attacks; Sudden Cardiac Arrest (SCA) caused by Ventricular Fibrillation (VF); and Ventricular Tachycardia (VT); which can be used by everyone, virtually everywhere, and at any time.

The apparatus according to the current invention, referred to hereinbelow as a "Rescue Cell", is an AED integrated into a handheld device such as mobile phone; pocket PCs, Personal Digital Assistant (PDA), smartphone, etc.

Rescue Cell device according to embodiments of the present invention is portable; it is integrated into a device that is in regular use by most people. A user of a Rescue Cell is likely to carry his Rescue Cell device with him during his daily routine and to have the device at hand most of the time. Thus, there is high likelihood of the Rescue Cell to be available to him in case of cardiac emergency to himself or to someone near him.

The Rescue Cell, according to embodiments of the present invention, disassembles to 3 parts.

The first part serves as a remote control for the AED so that the person operating the AED will be protected from getting an electrical shock himself while operating the apparatus.

The remote control may also be used to activate the local Emergency Medical Service (EMS), to provide information about location via Global Positioning System (GPS), and as a communication device between the person operating the AED and the EMS personnel.

Additionally and optionally, the remote control may provide visual, textual, animated or audio guidance and instruction to the user, guiding him during the rescue attempt.

Additionally and optionally, the remote control may monitor the rescue attempt and provide feedback and suggest corrective action to the user. For example, if the apparatus is not properly positioned on the patient, or if electrodes do not make proper contact with the patient, the apparatus may be able to detect the improper situation and suggest corrections.

Additionally and optionally, the remote control may provide information to the user regarding the success of the rescue attempt.

In case wherein the remote control is a cellular phone equipped with a stills or video camera, user may be instructed by EMS personnel to transmit a picture of the patient to be used by the EMS personnel to ensure proper placement of the apparatus on the patent. EMS personnel may guide the user by providing voice advise, guidance and reassurance.

The second part of the Rescue Cell device, according to embodiments of the present invention, is a Defibrillator Unit. The Defibrillator Unit comprises:

An energy storage (such as, but not limited to: an electrical battery such as Lithium battery, a fuel cell, and a rechargeable battery).

An electronic card that comprises:
High voltage charging power supply, using electrical power from the energy storage to generate high voltage.
High voltage capacitor, storing the generated high voltage.
High voltage discharge circuits, discharging stored high voltage, thus creating and shaping a defibrillation pulse.
An electronic analyzer circuit that analyzes the life threatening heart rhythm.
An electronic communication circuit that comprises preferably a bidirectional communication unit using communication technology such as infra red, RF (for example Bluetooth protocol) etc. to communicate with the remote part.
An incorporated electrode sensor pad with a defibrillator plate.
And a cord leading to the third part.

The electronics and battery parts optionally have shielding shock absorber protecting them from the high energy electric shock transmitted by the defibrillator plate.

The Defibrillator Unit is placed on the chest and is located on one side of the heart.

The third part of the Rescue Cell device, according to embodiments of the present invention, is the Second Electronic Pad unit.

The Second Electronic Pad unit comprises a second electrode sensor pad with a defibrillator plate.

The Second Electronic Pad unit is to be placed on the chest to be located on the other side of the heart.

The Defibrillator Unit and the Second Electronic Pad unit are connected by an electrical cable.

The Defibrillator Unit is connected to the Second Electronic Pad with an electric cord that is used for transmitting Electrocardiogram (ECG) signals from the Second Electronic Pad to the Defibrillator unit, and electric shock energy from the Defibrillator unit to the Second Electronic Pad. Optionally, ECG signals, or information derived from the ECG signals is wirelessly transmitted from the defibrillator unit to the remote control unit. Optionally, ECG signals, or information derived from the ECG signals is wirelessly transmitted from the remote control unit to EMS center. The EMS center may review the ECG signals, automatically or by a trained person, and provide further assistance to the user.

Using the current invention (an AED incorporated into a cellular phone) a person will be able to create his own "heart save environment" no matter where he is or where he goes to.

Advantages of the Invention include:

1. Rescue Cell device according to embodiments of the present invention is designed for use by everyone everywhere being a small and accessible device part of a regular and usable device such as mobile phone or other handheld device.

2. Rescue Cell device according to embodiments of the present invention use a separate sense and control units with a communication connection.

3. Rescue Cell device according to embodiments of the present invention incorporate the electronics pads with the defibrillator one in the other as a unit.

4. When Rescue Cell device incorporates a cellular phone, it is likely to be carried by the user, or be near the user at all or almost all times. In contrast to dedicated personal defibrillators, which people have tendency to leave at home or at their cars, the day to day usefulness of the mobile phone functionality, promotes having the device at close hand.

According to an exemplary embodiment of the current invention, a Rescue Cell apparatus having user functionality and cardiac defibrillation functionality, the apparatus comprising: a hand held device used as a remote control to a defibrillator unit, and further has user functionality selected from a group comprising: mobile phone; PDA, and media player; a defibrillator unit, wirelessly controlled by said hand held device, said defibrillation unit is constructed to sense ECG signals, and deliver a defibrillation pulse when attached to a patient; and a second electronic pad, connected with an electric cable to said defibrillator unit and used for sensing said ECG signals and delivering said defibrillation pulse when attached to a patient, wherein said hand held device, said defibrillator unit and said second electronic pad are adopted to be assembled to one unit when user functionality is used, and disassembled when defibrillation functionality is used.

In some embodiments the defibrillator unit comprises: at least first electrical pad, making electrical contact with said patient; an energy storage; an electronic card comprises: high voltage charging power supply, using electrical power from said energy storage to generate high voltage; high voltage capacitor, storing the generated high voltage; high voltage discharge circuits, discharging stored high voltage and delivering a defibrillation pulse to said patient via said first electrical pad and said second electronic pad; an electronic analyzer circuit, analyzing ECG signals of said patient; and a wireless communication circuit communicating with said hand held device.

In some embodiments the hand held device has mobile phone functionality. However, preferably the apparatus need not be connected to the cellular network in order to operate as a defibrillator. Alternatively, cellular functionality is missing.

In some embodiments the hand held device further has GPS functionality.

In some embodiments the hand held device communicates with emergency center via cellular communication channel.

In some embodiments the hand held device adopted to transmit to said emergency center its location.

In some embodiments the held device adopted to transmit to said emergency center information indicative of the ECG signal of said patient.

In some embodiments the hand held device adopted to provide operation instructions to the user of said apparatus.

In some embodiments the hand held device further comprising a camera, wherein said hand held device adopted to transmit to said emergency center images acquired by said camera.

In some embodiments the hand held device adopted to provide to the user instructions received from said emergency center.

In some embodiments the hand held device automatically alert said emergency center when abnormal ECG signal is detected and analyzed.

In some embodiments the hand held device adopted to enable delivery of defibrillation pulse only when abnormal ECG signal is detected and analyzed.

In some embodiments during defibrillation functionality operation, said hand held device is adopted to alert the user if any of first electrical pad and second electronic pad are not making proper electrical contact with said patient.

In some embodiments the charging level of said energy storage in said defibrillator unit is monitored by said hand held device used as a remote control to a defibrillator unit.

In some embodiments the hand held device further comprises an indicator, indicating charge level of said energy storage in said defibrillator unit.

In some embodiments the hand held device is adopted to alert the user when charge level of said energy storage; in said defibrillator unit drops below a predetermined level.

In some embodiments, the apparatus may be used by health care providing emergency rescue or law enforcement personnel. For example the apparatus may be used by policemen, ambulance crew, military nurse, etc.

According to another aspect of the current invention, a method of defibrillation is provided, the method comprising the steps of: dissembling a Rescue Cell apparatus having user functionality and cardiac defibrillation functionality to: a hand held device used as a remote control to a defibrillator unit, and further has user functionality selected from a group comprising: mobile phone; PDA, smartphone, and media player; a defibrillator unit, wirelessly controlled by said hand held device, said defibrillation unit is constructed to sense ECG signals, and deliver a defibrillation pulse when attached to a patient; and a second electronic pad, connected with an electric cable to said defibrillator unit and used for sensing said ECG signals and delivering said defibrillation pulse when attached to a patient, attaching said defibrillator unit to a first location on the chest of a patient; attaching said second electronic pad to a second location on the chest of a patient; acquiring ECG signal from said patient; analyzing said acquired ECG and determining cardiac fibrillation in said patient; and using said hand held unit to wirelessly control said defibrillator unit to deliver defibrillation pulse to said patient.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
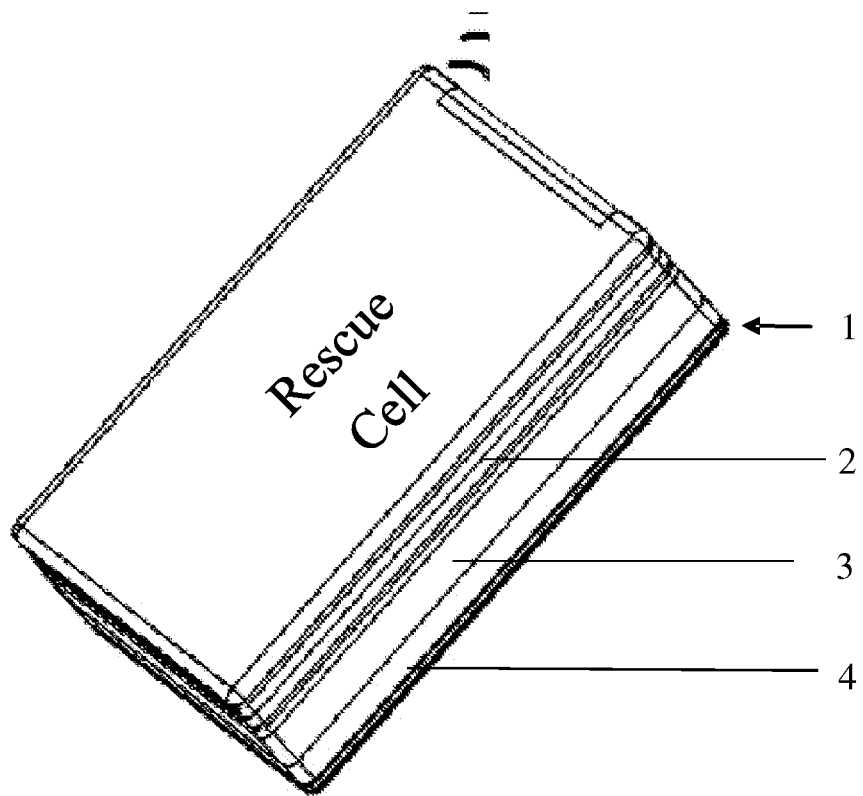
FIG. 1 schematically depicts an overview of the Rescue Cell apparatus in storage (or cell-phone use) configuration, according to an embodiment of the current invention.

The present invention relates to a mobile, hand-held apparatus for providing a solution for reducing deaths caused by Sudden Cardiac Arrest caused by Ventricular Fibrillation or Ventricular Tachycardia) to be used everywhere and at any time.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts. The drawings are generally not to scale.

For clarity, non-essential elements were omitted from some of the drawings. As used herein, an element or step recited in the singular and proceeded with the word "a" or "an" should be understood as not excluding plural elements or steps, unless such exclusion is explicitly recited.

FIG. 1 schematically depicts an overview of the Rescue Cell apparatus in storage (or cell-phone use) configuration.

Rescue Cell apparatus 1 according to embodiments of the present invention is an automated external defibrillator (AED) integrated with a handheld device such as mobile phone, pocket PCs etc.

Rescue Cell apparatus 1, according to embodiments of the present invention, is assembled from three parts that are easy to take apart.

Hand held device 2 is a mobile phone, smartphone, or a handheld computing device such as a Personal Digital Assistance (PDA) or a music player, such as MP3 player, with a defibrillator remote control unit. According to embodiments of the present invention hand held device 2 comprises a defibrillator remote control with regular handheld device unit functionality. In the non-limiting exemplary embodiment, hand held device 2 is a "flip to open" type cellular phone, however other types or cellular phones or other hand held devices may be used.

Handheld device unit 2 uses at least some of the regular handheld parts such as:

Digital processor with memory; Output devices such as a Screen and Speaker; input device such as Keyboard or Keypad; Camera, Battery; Global Positioning System receiver (GPS); Long Range communication unit (cellular); and Short range communication unit such as, but not limited to Infrared and Bluetooth, as known in the art. It should be noted that modern cellular phones are generally equipped with most or all these functions.

In the Rescue Cell apparatus the use of handheld device units 2 is the same as in any conventional handheld device—for example for making voice or video calls, sending and receiving e-mail, accessing the Internet, using camera for photography, etc.

Rescue Cell apparatus 1, according to embodiments of the present invention, may use handheld device unit 2 for additional other uses also such as:

In case of a sudden cardiac arrest, contacting a medical center and optionally a relative or a contact person.

Transmitting the location of handheld device using GPS data so that medical center and/or a contact person will be able to know the exact location of the patient. The medical service may than send a medical team to the known location and at the same time will follow the heart signs and give help and instructions to the user.

Figure 2:
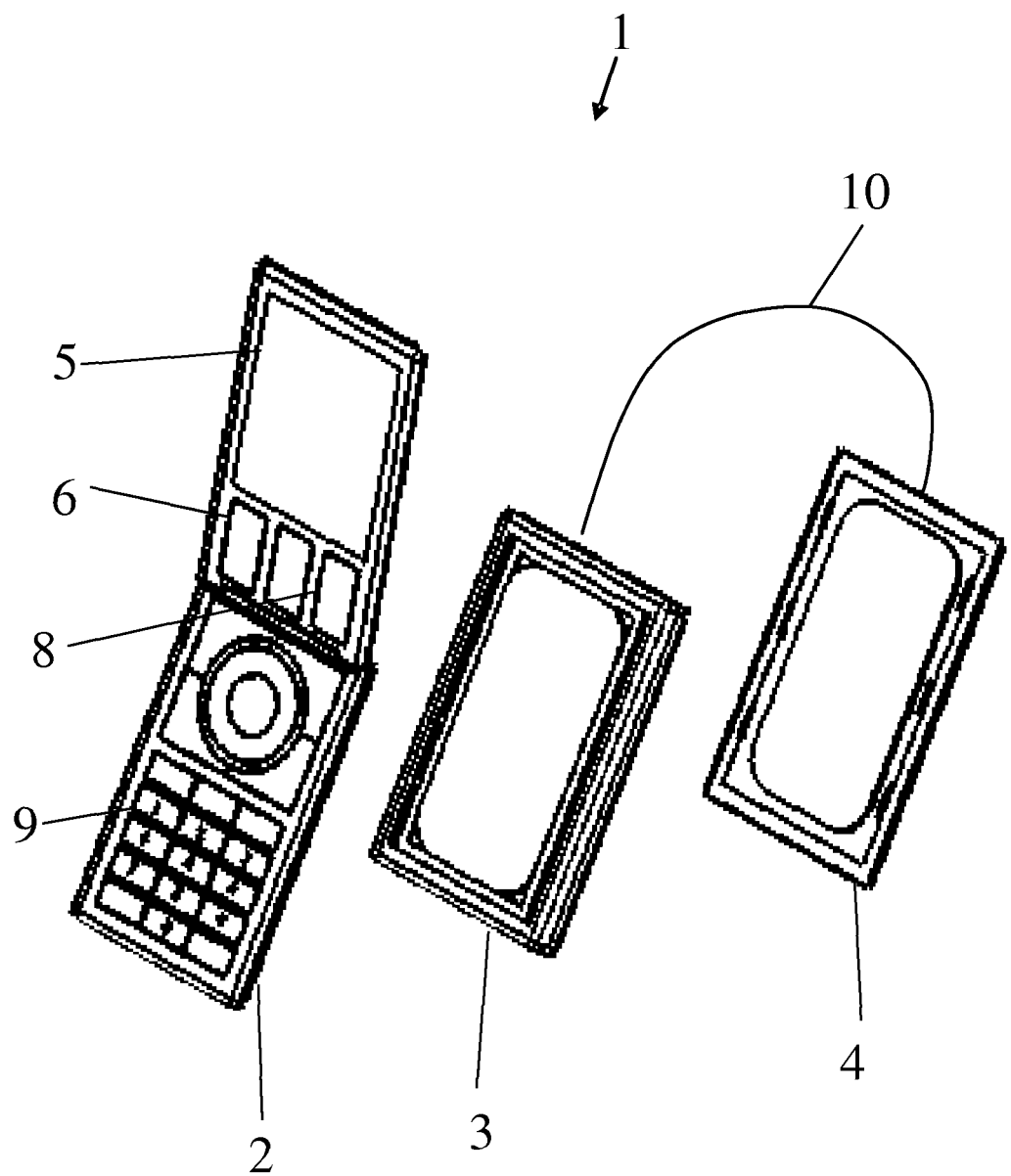
FIG. 2 schematically depicts the Rescue Cell apparatus in a disassembled configuration.

FIG. 2 schematically depicts the Rescue Cell apparatus 1 in a disassembled configuration showing the handheld device unit 2; the defibrillator unit 3; and the second electronic pad unit 4.

On handheld device unit 2, when used as remote control unit for defibrillator unit 3, there are preferably two dedicated keys for defibrillator use. Preferably these keys are big and colored for easy use. Optionally, these keys are dedicated keys on the hand held device unit, however, the keys may be keys used for other functions during normal operation of the handheld device unit. For example, the numeral 1, and 2, normally used for dialing a phone number in a cellular phone may be redefined as the two keys used for operating the remote control unit when the handheld device unit 2 is used for rescuing a patient. Optionally, when touch-sensitive screen is used, the application running the remote controlling program will display these keys on the screen.

It should be noted that in some embodiments handheld device unit 2 is a dedicated device specifically constructed for the use as a remote control for the Rescue Cell. In this case, dedicated keys 6 and 8 are integrated into it.

In other embodiments, handheld device unit 2 is a modified device specifically modified for the use as a remote control for the Rescue Cell. In this case, dedicated keys 6 and 8 may be added to it. Alternatively, the modification comprises replacing the keyboard or otherwise marking keys 6 and 8.

In yet another embodiment, handheld device unit 2 is a hand held device having additional software specifically programmed for the use as a remote control for the Rescue Cell. In this case, keys normally used for other functions may be used as keys 6 and 8 may be added to it.

When a user notices a possible cardiac emergency, he presses the "cardiac rescue activation" key 6 which activates the cardiac rescue mode of the Rescue Cell apparatus 1. In some embodiments, the user performs "cardiac rescue activation" in ways similar to activation of other routines of a hand held devices, for example pressing a specific key for long duration, or flipping through menus.

Preferably, an output device on handheld device unit 2, for example screen 5 and preferably a speaker (not indicated in the figures) serves to instruct the user to perform the following steps:

1. The user is instructed to disassemble Defibrillator Unit 3 and second electronic pad unit 4 from handheld device unit 2. Activating cardiac rescue mode by pressing activation key 6 and/or disassembling Rescue Cell apparatus 1 turns on the short range communication between Defibrillator Unit 3 and handheld device unit 2 and optionally activates sensing electronics within Defibrillator Unit 3. Optionally, activation key 6 is missing and activation of rescue mode is done by disassembling the Rescue Cell apparatus 1

Figure 6:
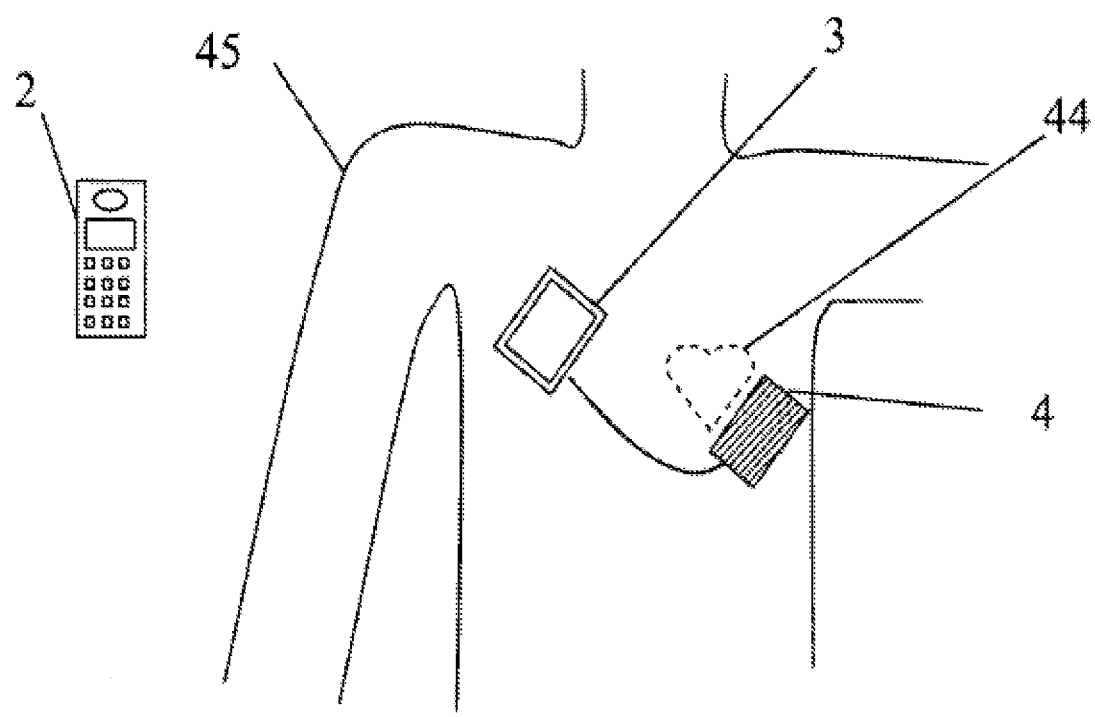
FIG. 6 schematically depicts optional positioning of Second Electronic Pad unit and Defibrillator unit in relation to a patient.

2. The user is instructed to place Defibrillator Unit 3 and second electronic pad unit 4 on the patient's chest, as seen in FIG. 6. It should be noted that the locations of Defibrillator Unit 3 and second electronic pad unit 4 over to the patient's heart 44 is important, but location of the two units may be exchanged. Preferably, Defibrillator Unit 3 and second electronic pad unit 4 make electrical contact with the patient's skin.

After placing Defibrillator Unit 3 and second electronic pad unit 4 on the patient chest, the on/off (preferably colored green) button 6 is pressed. In some embodiments, Defibrillator Unit 3 and second electronic pad unit 4 are held in place using a belt (not shown in the figures). Additionally or alternatively, Defibrillator Unit 3 and second electronic pad unit 4 are optional held in place using adhesive. For example, an adhesive may be applied, but preferably is already present but is covered with a protective cover layer which is removed before attaching the Defibrillator Unit 3 and second electronic pad unit 4 in place. Optionally, said adhesive is also used for enhancing the electric contact between said Defibrillator Unit 3 and second electronic pad unit 4 and the patient, however, the function of adhesion and electrical contact enhancement may be performed by two different materials.

According to an exemplary embodiment, a remote control voice informs the user that cardiac signals are being analyzed. If a Ventricular Fibrillation (VF) or Ventricular Tachycardia (VT) conditions were analyzed, the remote control output serves to ask the user to press shock (preferably colored red) button 8 for delivering a defibrillation pulse to the patient.

If the on/off (green) button 6 was pressed and the rhythm analysis did not detect VF or VT condition, the remote control will not ask the user to press the Shock button.

Optionally, a camera on handheld device is used for sending a photo of the patient to be sure that pads parts: parts 3 and 4 are in the correct place like shown in the FIG. 6.

Optionally, handheld device unit 2 transmits a warning to an EMS center that the rescue mode was activated. Optionally EMS personnel respond by communicating with the user using the long range communication channel of handheld device unit 2.

3. In some embodiments, Defibrillator Unit 3 senses the placement of Defibrillator Unit 3 and second electronic pad unit 4 on the patient chest, for example by measuring electrical resistance between electrodes on Defibrillator Unit 3 and second electronic pad unit 4 on the patient chest. In this case, ECG analysis commences as soon as ECG signal is detected.

Once ECG is detected and VF or VT are diagnosed, Defibrillator Unit 3 communicates the diagnosis to handheld device unit 2. Defibrillation action is attempted.

If ECG is detected, and it is diagnosed as normal, or not a state of VF or VT, the user is instructed to take other corrective actions such as bringing the patient to a nearby hospital and/or to monitor the patient.

Optionally, handheld device unit 2 transmits the diagnosis or the ECG signal or both to the EMS center.

Optionally, if after a sensing electrical resistance between electrodes on Defibrillator Unit 3 and second electronic pad unit 4, no ECG is detected, the Defibrillator Unit 3 communicates the no ECG condition to handheld device unit 2. Handheld device unit 2 may instruct the user to verify proper placement of Defibrillator Unit 3 and second electronic pad unit 4. Following user verification of proper placement of Defibrillator Unit 3 and second electronic pad unit 4, if no ECG is found, defibrillation may be attempted.

4. If defibrillation action is necessary, the user is instructed to avoid physical contact with the patient and press the Shock (preferably colored red) button 8 for sending a defibrillation pulse.

5. Preferably, the Defibrillator Unit 3 continues to monitor the ECG signal from the patient and steps 3 and 4 are repeated if normal ECG signal is not detected or AF reappears. Optionally, a second defibrillation pulse is delivered with higher pulse energy if the first defibrillation pulse did not restored safe cardiac activity. However, it should be noted that due to the small size of the device, battery in Defibrillator Unit 3 may supply energy to only few and possibly only one defibrillation actions.

It should be noted that preferably, Rescue Cell apparatus 1 may be operated without need for communication with the EMS center. Specifically, it is preferable that operation is possible at location where long range communication is interrupted or unavailable, for example when the user is out of range from any cellular antenna such as in elevator or a tunnel, etc.

Optionally the medical center may read the heart analysis and if required, the medical center is able also to remotely activate the defibrillator by sending defibrillation commands.

A battery in the handheld device with a defibrillator remote control unit is preferably a conventional battery used by handheld device unit 2. Preferably, whenever the handheld device is connected to an outside power source, both batteries are charged. In normal operation, the battery in the Defibrillator Unit 3 is not used for normal operation of hand held unit 2, such as using the device 1 as mobile phone or using its other functions—ensuring that the battery of Defibrillator Unit 3 is fully charged and has enough stored energy for delivering defibrillation pulse. However, optionally, if the battery in the hand held remote device unit 2, battery in Defibrillator Unit may be used for charging or partially charging the battery in the hand held unit 2.

The communication protocol used between hand held device 2 and defibrillator unit 3 can be the handheld device communication such as Bluetooth or a dedicated communication unit.

The handheld device with a defibrillator remote control unit communication is used for communication with the defibrillator part 3. The use of a remote control unit is for safe user environmental. If the user of the Rescue Cell Device is not the patient himself, the user will be safe from getting a shock administered to the patient.

Figure 3:
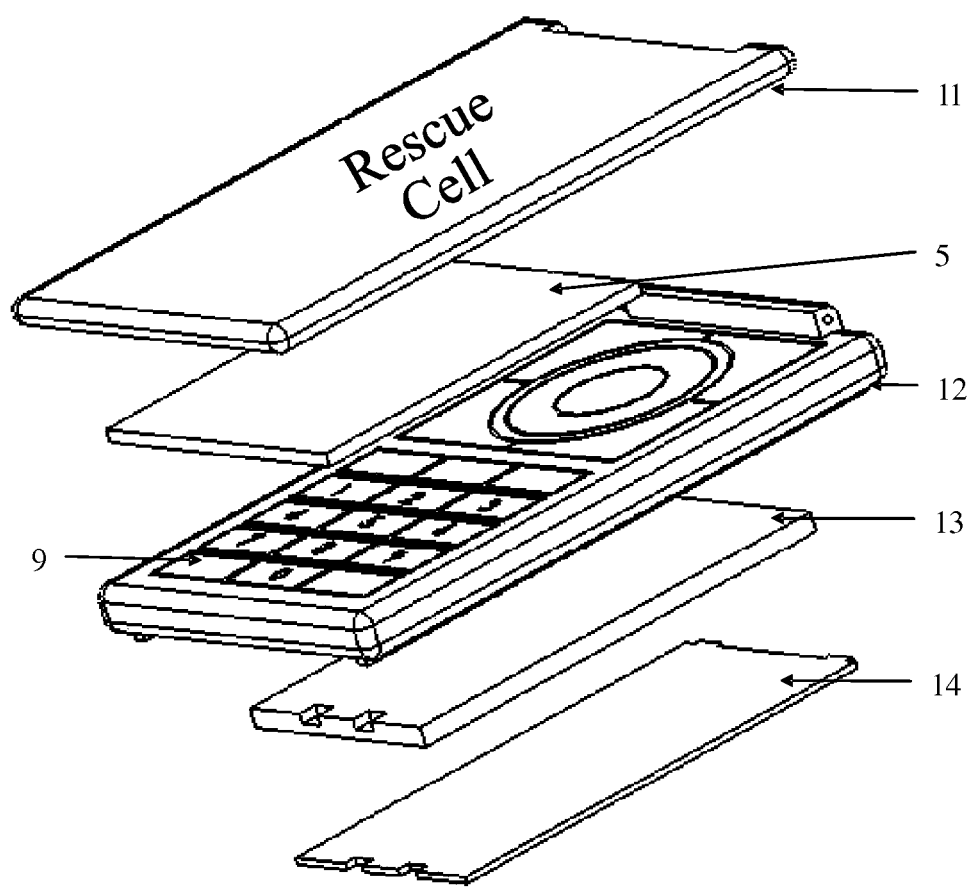
FIG. 3 schematically depicts some details of the or hand held device with a defibrillator remote control Unit, according to an embodiment of the current invention.

FIG. 3 schematically depicts details of the Mobile Phone or Handheld device with a defibrillator remote control Unit 2 according to an exemplary embodiment of the current invention.

FIG. 3 shows: Screen 5; Keyboard 9; Cover 1; the body of the mobile phone or other handheld device 12; Battery 13; and Battery Cover 14.

Figure 4:
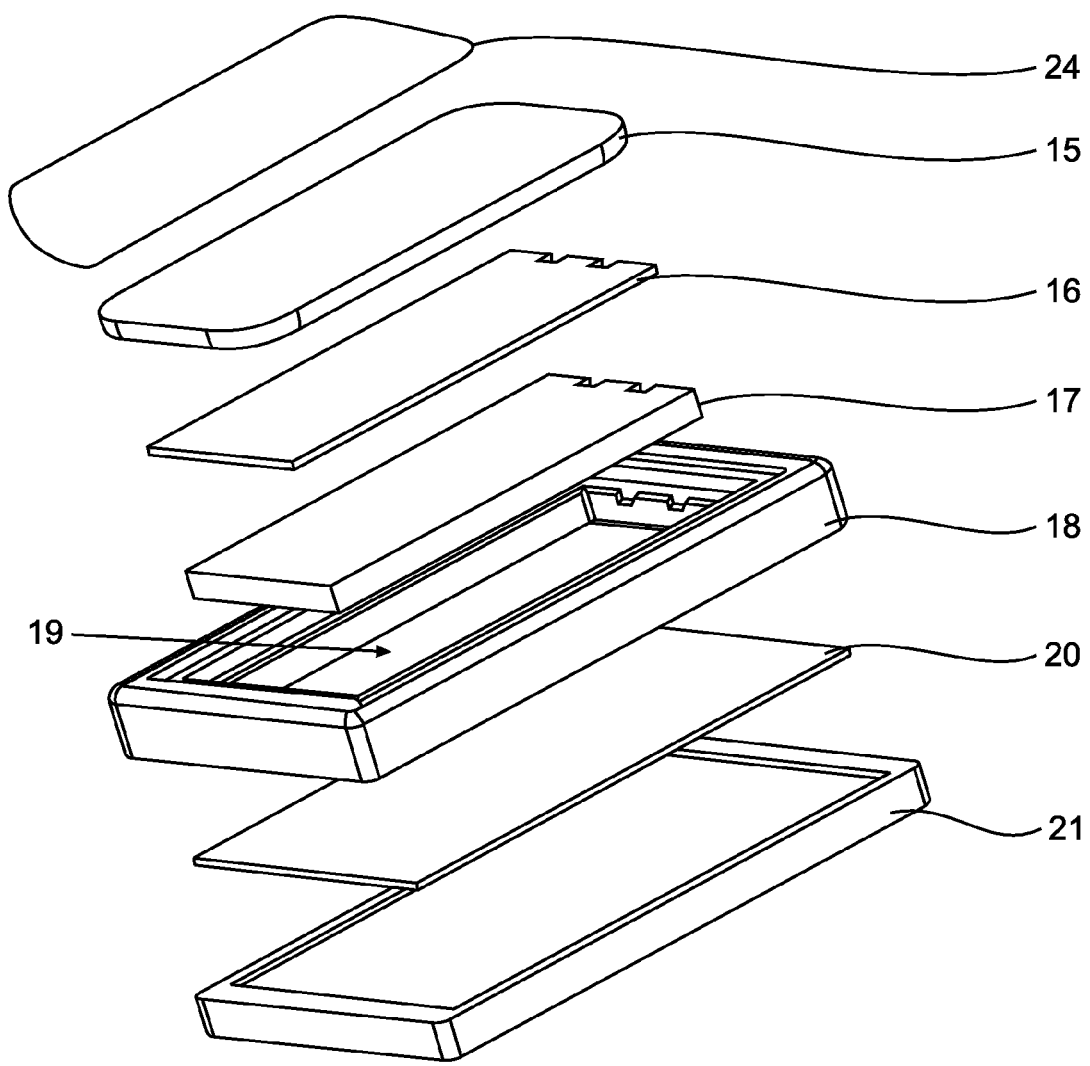
FIG. 4 schematically depicts some details of the Defibrillator Unit, according to an embodiment of the current invention.

FIG. 4 schematically depicts some details of Defibrillator Unit 3 according to an exemplary embodiment of the current invention.

Defibrillator Unit 3 according to an exemplary embodiment of the current invention includes an electronic sensor pad 15 placed on one side of heart 44 of a patient 45 after removing the electronic sensor pad cover 24.

Electronic sensor pad 15 receives cardiac information from the patient and optionally delivers defibrillator pulse to the patient. However, separate electrodes, one for sensing and one for defibrillation may be present in pad 15.

Defibrillator unit 3 according to embodiments of the present invention includes a defibrillator battery 17. Defibrillator battery 17 is preferably placed inside a defibrillator battery housing 19 and covered with a defibrillator battery cover 16.

The use of a separate battery for the defibrillator unit and the handheld device ensures a full battery charge for defibrillation use so that regardless of the handheld device battery use, the defibrillator has sufficient power to give shocks. The use of separate batteries enables separation of defibrillator unit 3 from the handheld device 2.

Defibrillator unit 3 according to embodiments of the present invention comprises an electronic card 20 that comprises short range communication unit to communicate with the remote control unit 2 to send the cardiac signal analysis from the patient and to get control commands from the control unit 2. Electronic card 20 is covered with Electronic Card Cover 21.

Defibrillator unit 3 analyzes a potentially life threatening cardiac arrhythmias of ventricular fibrillation and ventricular tachycardia to know if shock is needed.

Electronic card 20 and defibrillator battery 17 in defibrillator unit 3 are placed in a defibrillator unit case 18. Preferably, case 18 includes shielding and a shock absorber such as silicon rubber or foam or conductive layer so that the case not be affected from the defibrillator shock.

Defibrillator unit 3 is placed on one side of the heart as depicted in FIG. 6.

Rescue Cell device 1 according to embodiments of the present invention includes second electronic sensor pad 4. The second electronic sensor pad includes an electronic sensor pad 22 placed on the other side of the heart. Electronic sensor pad 22 with second electronic sensor pad 15 connect with an electrical wire 10 to deliver the defibrillator pulse. The two pads are to be placed on two sides of the heart.

Figure 5:
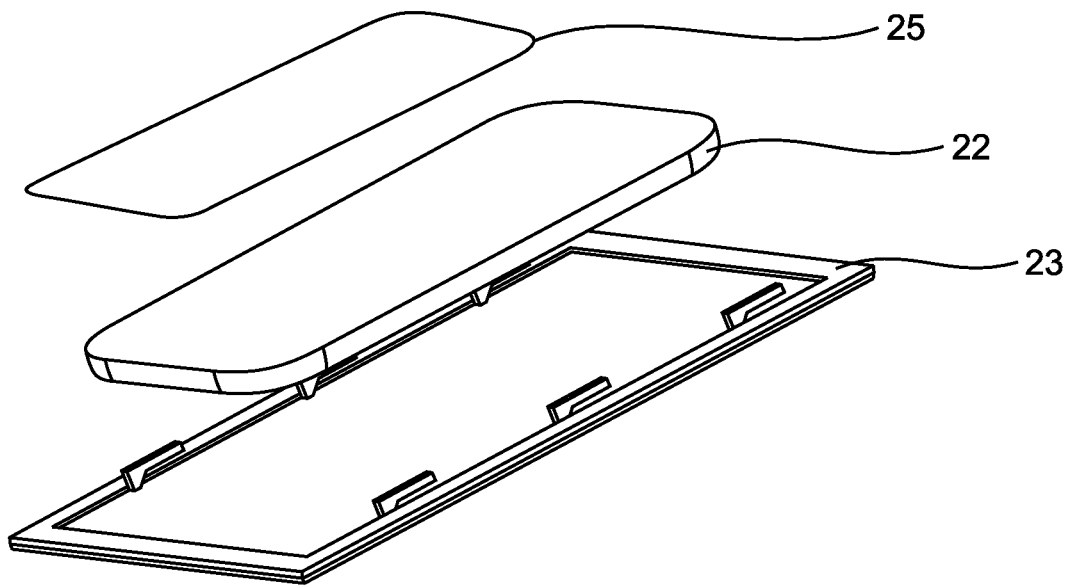
FIG. 5 schematically depicts details of the second electronic pad unit, according to an embodiment of the current invention.

FIG. 5 schematically depicts some details of the Second Electronic Pad unit 4 according to an exemplary embodiment of the current invention.

Second electronic pad unit 4 according to an exemplary embodiment of the current invention comprises an electronic sensor pad 22. Electronic Sensor pad 22 is used for delivering defibrillation pulse and for sensing cardiac ECG signal. However, electronic sensor pad 22 may comprise two separate electrodes, one for sensing and one for defibrillation.

Electronic sensor pad 22 is preferably covered with electronic sensor pad cover 25. Electronic sensor pad 22 is connected to defibrillator unit 3 by wire 10 (not shown in the figure).

In assembled configuration, wire 10 is preferably folded within the apparatus and is deployed when Second Electronic Pad unit 4 is separated from Defibrillator Unit 3.

FIG. 6 schematically depicts optional positioning of second electronic pad unit 4 and defibrillator unit 3 in relation to heart 44. However, other locations are possible, for example: one unit on the chest—directly over the heart and one on the back.

Figure 7:
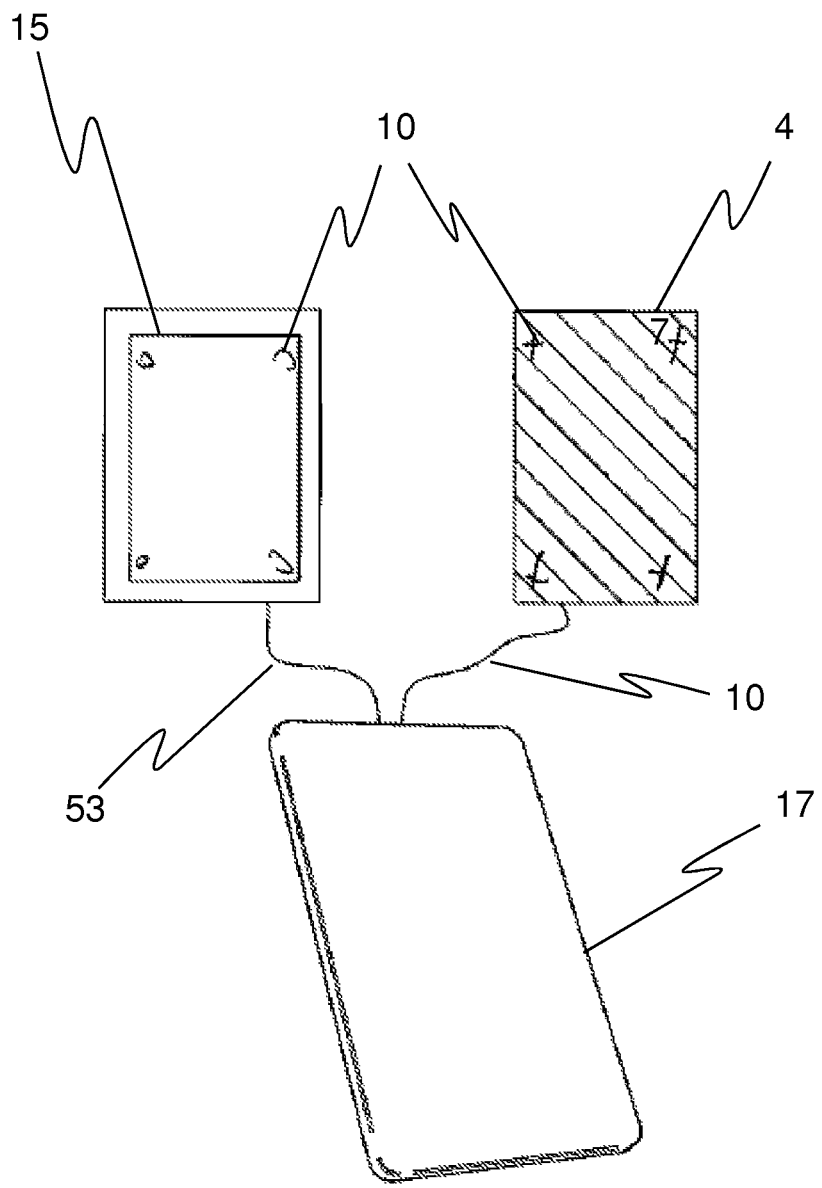
FIG. 7 is a pictorial representation of the sensor electronic pad (as part of the defibrillator unit) and second electronic pad unit configurable with the defibrillator battery, in accordance with an embodiment of the current invention.

Optionally or alternatively, Rescue Cell device 1 comprises sensor electronic pad 15 (as part of defibrillator unit 3) and second electronic pad unit 4 (both collectively referred to hereinbelow as "power pads") configurable with defibrillator battery 17. Defibrillator battery 17 is electrically connected to sensor electronic pad 15 and second electronic pad unit 4 by wires 10, as shown in FIG. 7, as noted hereinabove. Defibrillator battery 17 additionally has appended communication capability, as described hereinbelow. Apart from differences described below, Rescue Cell device 1 is identical in notation, configuration, and functionality to that shown in FIGS. 1 and 4, and elements indicated by the same reference numerals and/or letters are generally identical in configuration, operation, and functionality as described hereinabove. The power pads have a plurality of orientation markings 55—typically at each corner as shown in the figure—as is described further hereinbelow.

Figure 8:
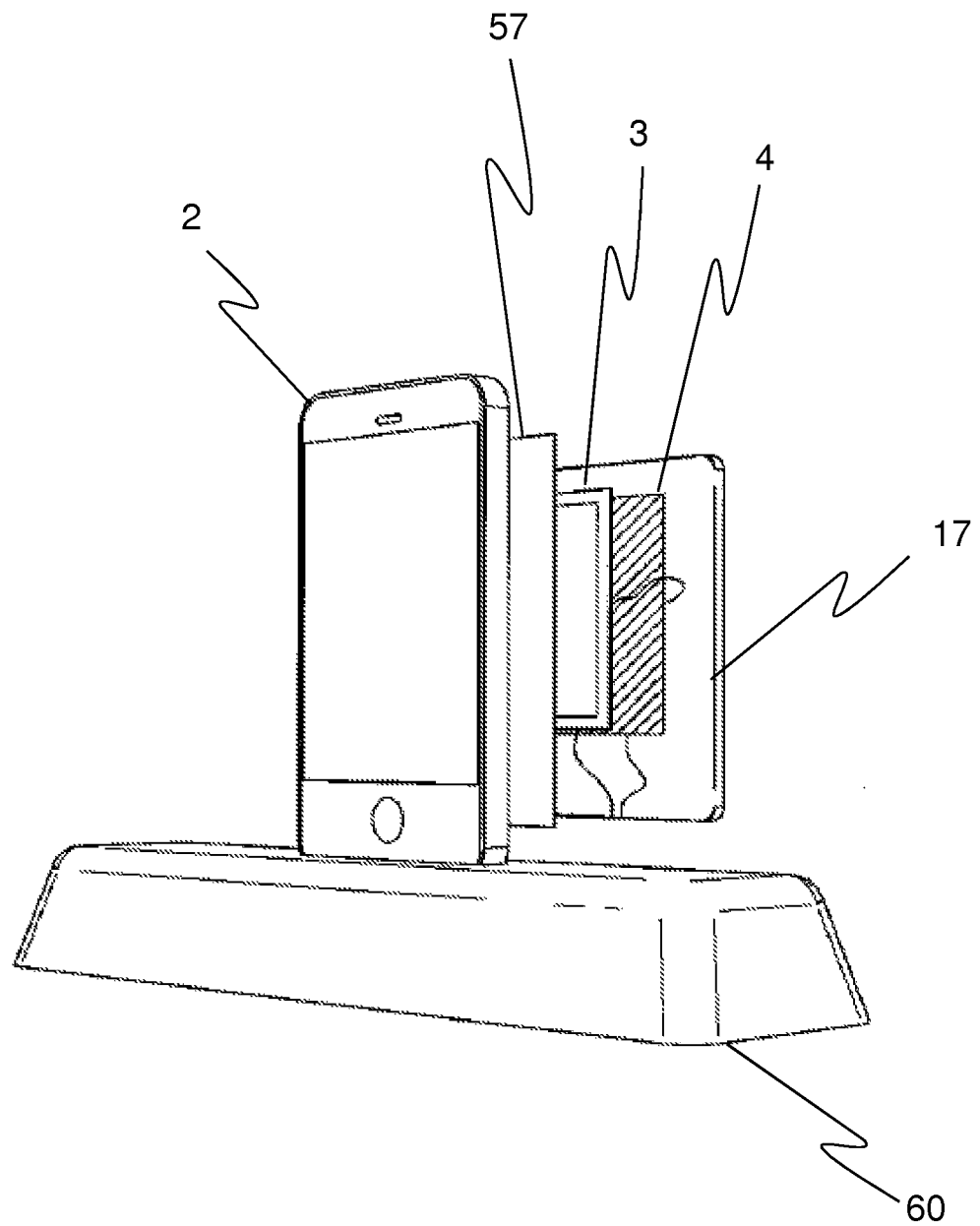
FIG. 8 is a pictorial representation of the handheld device, the power pads, the defibrillator battery, and a retaining cover configured to be held within a cradle, in accordance with an embodiment of the current invention.

In another optional or alternative configuration of Rescue Cell device 1, as shown in FIG. 8, handheld device 2, sensor electronic pad 15 (part of defibrillator unit 3, not shown in the figure), second electronic pad unit 4, defibrillator battery 17, and a retaining cover 57 are configured to be held within a cradle 60. Apart from differences described below, Rescue Cell device 1 is identical in notation, configuration, and functionality to that shown in FIGS. 1, 4, and 7, and elements indicated by the same reference numerals and/or letters are generally identical in configuration, operation, and functionality as described hereinabove. When in a stored configuration, sensor electronic pad 15, second electronic pad unit 4, defibrillator battery 17, and a retaining cover 57 are configured together, as described hereinabove in defibrillator unit 3.

Cradle 60 has an integrated communication unit (not shown in the figure) to allow GPS detection and for communication with defibrillator battery 17, as described hereinbelow. Cradle 60 is connected to mains electricity (not shown in the figure) and the cradle typically provides electrical power to maintain the electrical charge of defibrillator battery 17, as known in the art. Additionally or optionally, cradle 60 may hold the handheld device (and thereby maintain the electrical charge of the handheld device) or only sensor electronic pad 15, second electronic pad unit 4, defibrillator battery 17, and a retaining cover 57.

Whereas handheld device 2 (typically a smartphone, as noted hereinabove) is relatively expensive and is typically carried by most people, cradle 60 is lightweight and inexpensive. As part of rescue cell device 1, a plurality of cradles may be deployed in workplace and public commerce locations, such as but not limited to: office environments; other workplaces; and stores. Additionally, sensor electronic pad 15, second electronic pad unit 4, defibrillator battery 17, and a retaining cover 57 are all relatively inexpensive and may be deployed with the plurality of cradles. Deployment of cradle 60 with defibrillator unit 3 elements noted hereinabove, in many locations allows a network of rescue cell devices to be readily/immediately available for defibrillation, as further described below.

Figures 9A, 9B:
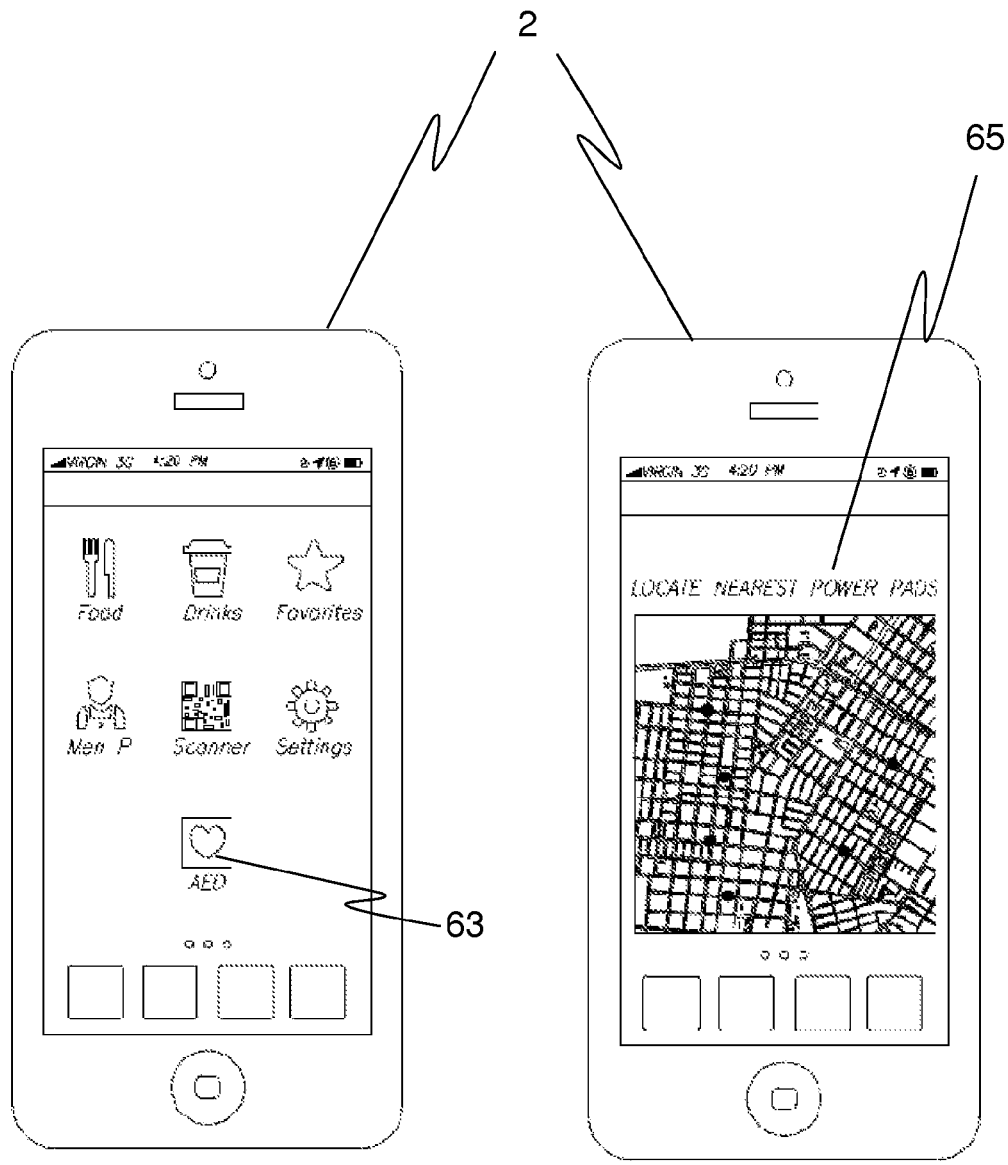
FIGS. 9A and 9B are schematic representation of the handheld device with a rescue cell application and a generated location map, respectively, in accordance with an embodiment of the current invention.

Reference is currently made to FIGS. 9A and 9B which show pictorial representations of handheld device 2 with a rescue cell application 63 and a generated location map 65, respectively, in accordance with an embodiment of the current invention. Rescue cell application 63 is installed on mobile device 2, as known in the art. Among other functions of rescue cell application 63 has the ability to interact with a GPS system and to locate the nearest cradle 60 having power pads and the charged battery—for near-immediate defibrillation use. Location map 65 is an exemplary display useful in guiding the user to cradle 60 location.

Once deployed cradle 60 with power pads and defibrillator battery 17 are located, as described hereinabove, elements of rescue cell device 1 are positioned on the patient in preparation for defibrillation, as described both previously and hereinbelow.

Figure 10:
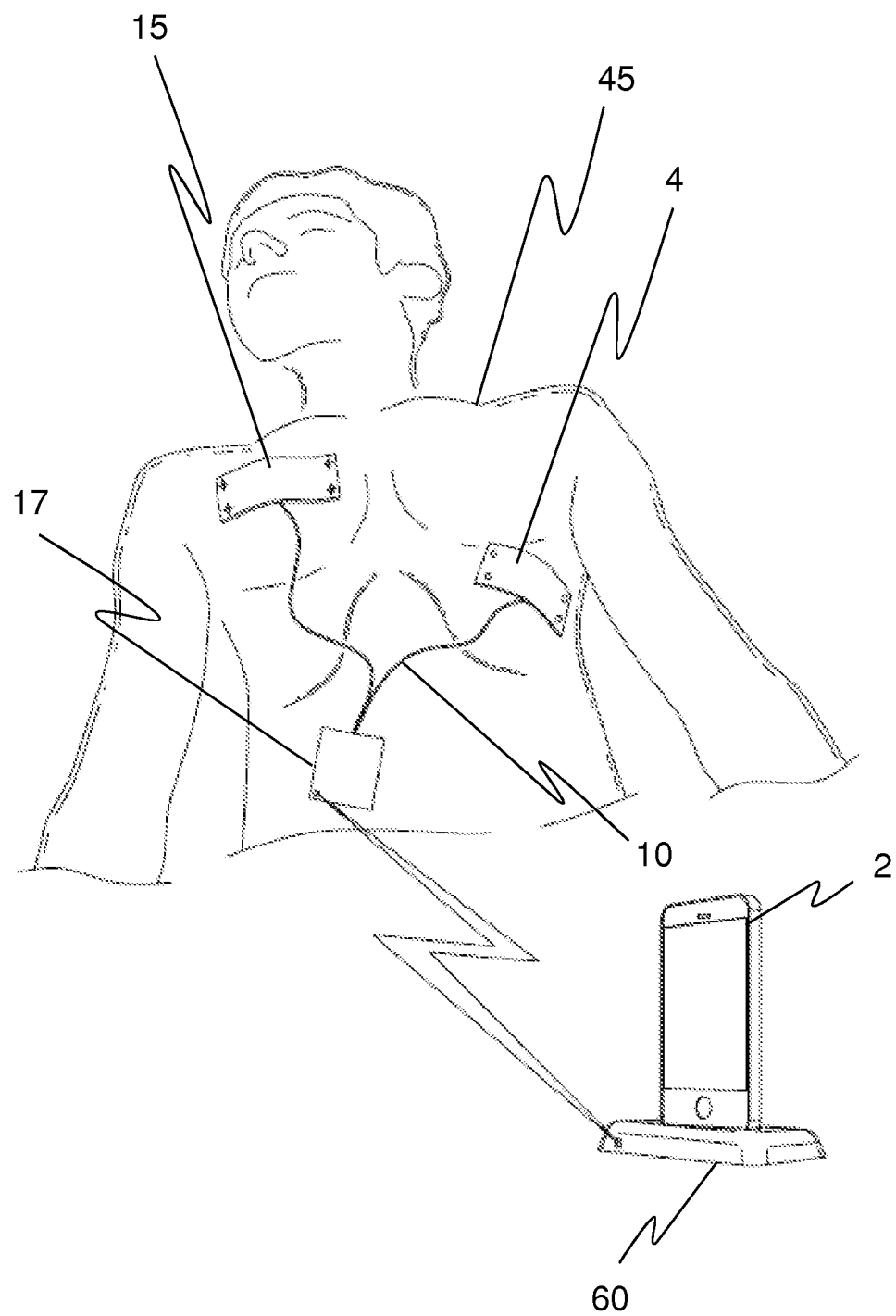
FIG. 10 is a pictorial representation of the patient with elements of the rescue cell device positioned on the patient, in accordance with embodiments of the current invention.

Reference is currently made to FIG. 10, which is a pictorial representation of patient 45 with elements of rescue cell device 1 positioned on the patient, in accordance with embodiments of the current invention. Apart from differences described below, rescue cell device 1 is identical in notation, configuration, and functionality to that shown in FIGS. 1, 4, 7, and 8, and elements indicated by the same reference numerals and/or letters are generally identical in configuration, operation, and functionality as described hereinabove. In the present figure, hand held device 2 is shown mounted in cradle 60 and remote control of defibrillation is performed through from cradle 60 to battery 17, as described hereinabove. Alternatively or optionally, remote control of defibrillation is performed using hand held device 2—not mounted in cradle 60—the hand held device communicating to battery 17.

In an emergency situation, typical of that for a defibrillation setting, the person or persons performing defibrillation may not be familiar with or may not be well trained in using rescue cell device 1. In other embodiments of the present invention described hereinabove, the hand held device is used to communicate with remote emergency personnel to receive guidance and/or feedback.

In another embodiment of the present invention, as described hereinbelow, the hand held device is used to provide immediate image recognition feedback to the user to verify power pad placement, without the need for telecommunication. This capability is especially important, inter alia, in a situation where—for whatever reason—telecommunication is not possible and/or practical.

Figure 11:
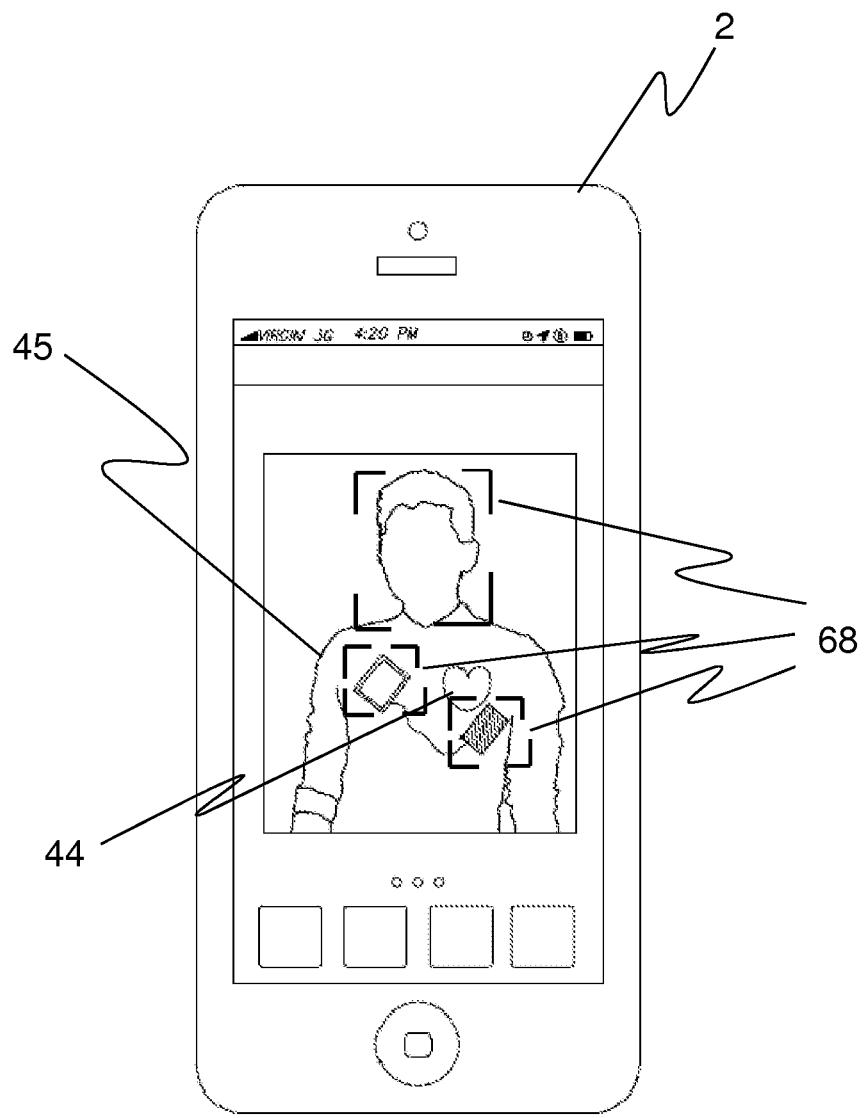
FIG. 11 is a pictorial representation of the handheld device displaying the patient and elements of the rescue cell device positioned on the patient, as shown in FIG. 10, in accordance with embodiments of the current invention.

Reference is currently made to FIG. 11, which is a pictorial representation of handheld device 2 displaying patient 45 and elements of rescue cell device 1 positioned on the patient, as shown in FIG. 10, in accordance with embodiments of the current invention. Apart from differences described below, rescue cell device 1 is identical in notation, configuration, and functionality to that shown in FIGS. 1, 4, 7, 8, 9, and 10 and elements indicated by the same reference numerals and/or letters are generally identical in configuration, operation, and functionality as described hereinabove.

Handheld device 2 views patient 45 through a camera and with associated image recognition capability—hereinbelow called an "image recognition module"—typically present in exemplary smartphones. Patient 45 and elements of rescue cell device 1 positioned on the patient, as shown in FIG. 10, are displayed—as shown schematically in FIG. 11.

The image recognition module, using image recognition capability—either present in hand held device 2 or as part of rescue cell application 63 (ref FIG. 9A)—is used to identify patient physiological features, such as but not limited to: patient's face, patient's shoulders, and patient's nipples and to verify positioning of power pads to heart 44 on the patient with regard to patient physiological features. Image recognition is also performed using the orientation markings on power pads (ref FIG. 7) to further verify power pad positioning on the patient. Image recognition symbols 68 schematically indicate verified power pad positioning on the patient, allowing defibrillation to proceed. If power pads are not properly positioned, the user is prompted to reposition one or both power pads before proceeding.

An exemplary method of using rescue cell 1, in accordance with an embodiment of the current invention includes:

1. Using the handheld device to locate the nearest/most convenient cradle with defibrillator unit having power pads and battery—as described hereinabove.
2. Positioning elements of the rescue cell on the patient—namely power pads and battery—to ready them for defibrillation.
3. Verifying the positioning of the power pads using the image recognition module—as described hereinabove—before defibrillation; and readjusting power pads if necessary.
4. Performing defibrillation, as described hereinabove.

For clarity, the person operating the device is not shown in this figure. However, it is understood that hand held unit 2 is operated by a user. Alternatively, the hand held unit may be activated and connected by the patient at onset of the attack, when the patient is in at least partial physical and mental ability and the defibrillation is activated fully automatically.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A rescue cell apparatus used for cardiac defibrillation of a patient, the apparatus comprising:
    a hand held device for sending and receiving communication signals and configured to be used as a remote control to transmit a defibrillator signal to administer a defibrillation pulse to the patient for cardiac defibrillation;
    a defibrillator unit having a sensor electronic pad positioned on the patient, the sensor electronic pad configured to receive the defibrillator signal and to deliver the defibrillation pulse;
    a second electronic pad, connected by an electrical wire to the defibrillator unit, the second electronic pad positioned on the patient- and configured to detect ECG signals and to receive the defibrillator signal to deliver the defibrillation pulse to the patient;
    an image recognition module configured in the handheld device, and further configured to verify positioning of the sensor electronic pad and the second electronic pad on the patient before cardiac defibrillation; and
    a plurality of cradles configured to be deployed in workplace and public commerce locations, with respective cradles configured to hold at least the defibrillator unit and the second electronic pad,
    wherein the handheld device is configured to locate at least one of the plurality of cradles for substantially immediate use in cardiac defibrillation.

2. The apparatus of claim 1, wherein the image recognition module is further configured to utilize patient physiological features to verify positioning of the sensor electronic pad and the second electronic pad.

3. The apparatus of claim 2, wherein the defibrillator unit further comprises:
    a battery;
    an electronic card comprising:
        a high voltage charging power supply configured to use electrical power from the battery to generate a high voltage charge;
        a high voltage capacitor, configured to store the generated high voltage charge;
        high voltage discharge circuits, configured to discharge the stored high voltage charge and to deliver the defibrillation pulse to the patient via the sensor electronic pad and the second electronic pad;
        an electronic analyzer circuit, configured to analyze ECG signals measured from the patient; and
        a wireless communication circuit configured to enable communication with the hand held device and with at least one of the plurality of cradles.

4. The apparatus of claim 3, wherein at least one of the plurality of cradles is configured to communicate with the wireless communication circuit of the defibrillator unit.

5. The apparatus of claim 2, wherein the hand held device is configured to communicate with an emergency center via a cellular communication channel.

6. The apparatus of claim 2, wherein the hand held device further has a rescue cell application configured to use GPS functionality of the hand held device.

7. The apparatus of claim 6, wherein the hand held device is configured to indicate its location to the emergency center.

8. The apparatus of claim 2, wherein the hand held device is configured to transmit information indicative of the ECG signal of said patient to the emergency center.

9. The apparatus of claim 2, wherein the hand held device is configured to provide operation instructions for use of the apparatus, chosen from the list including: audible instructions and visual instructions.

* * * * *